(12) United States Patent
Yamagata et al.

(10) Patent No.: US 6,187,334 B1
(45) Date of Patent: Feb. 13, 2001

(54) FOODS FOR PREVENTING VOMITING

(75) Inventors: Norimitsu Yamagata, Tama; Hiroshi Tanaka; Yoshinori Hamachiyo, both of Hino; Hiroko Ito, Musashino; Kazuhiko Kaneda, Setagaya-Ku, all of (JP)

(73) Assignee: Kewpie Kabushiki Kaisha, Tokyo-To (JP)

( * ) Notice: Under 35 U.S.C. 154(b), the term of this patent shall be extended for 0 days.

(21) Appl. No.: 09/530,993

(22) PCT Filed: Sep. 6, 1999

(86) PCT No.: PCT/JP99/04821

§ 371 Date: May 9, 2000

§ 102(e) Date: May 9, 2000

(87) PCT Pub. No.: WO00/13529

PCT Pub. Date: Mar. 16, 2000

(30) Foreign Application Priority Data

Sep. 9, 1998 (JP) .................................................. 10-254933
Dec. 18, 1998 (JP) .................................................. 10-361329

(51) Int. Cl.⁷ .......................... A61K 47/00; A61K 38/00; A01N 37/18; C07K 1/00; C07K 5/00

(52) U.S. Cl. .......................... 424/439; 530/300; 530/350; 514/2; 514/12

(58) Field of Search .......................... 514/2, 12; 424/439; 530/300, 350

(56) References Cited

FOREIGN PATENT DOCUMENTS

| 2-36123 | 2/1990 | (JP) . |
| 11-9222 | 1/1999 | (JP) . |
| 11009222 | * 1/1999 | (JP) .................................. A23L/1/30 |
| 96/30367 | 10/1996 | (WO) . |

* cited by examiner

Primary Examiner—Avis M. Davenport
(74) Attorney, Agent, or Firm—Wenderoth, Lind & Ponack, L.L.P.

(57) ABSTRACT

The present invention relates to an antiemetic food product comprising a solution containing one or more thickeners selected from low-methoxyl pectin, sodium alginate, alginic acid, kappa carrageenan, iota carrageenan, lambda carrageenan and gellan gum, to an antiemetic food product comprising, as one set, a solution containing any of these thickeners, and typically a calcium solution, and to a method for preventing a patient from suffering from emesis associated with the ingestion of liquid food, comprising feeding the antiemetic food product to the patient.

11 Claims, No Drawings

FOODS FOR PREVENTING VOMITING

TECHNICAL FIELD

The present invention relates to antiemetic food products. More particularly, the present invention relates to food products useful for preventing "emesis", a typical adverse effect that afflicts those patients who are ingesting nutrition from liquid food. The present invention also relates to a method for preventing patients from suffering from emesis associated with the ingestion of liquid food, comprising feeding the above antiemetic food products to the patients.

BACKGROUND ART

Most patients who are ingesting nutrition from liquid food or a liquid diet are weak, and this inhibits the delivery of food contained in the stomach to the small intestine. Therefore, they tend to vomit when their stomachs are filled with a certain amount of liquid food.

In order to prevent these patients from suffering from emesis of this type, the following methods have conventionally been adopted: a method in which the rate of feeding liquid food to the patients is decreased; a method in which the amount of liquid food to be fed is decreased; a method in which liquid food is diluted to promote its flow from the stomach to the small intestine; and a method in which the patients are encouraged to sit in a position considered to be ideal. Other methods have also been adopted in which medicines are used to assist the delivery of liquid food from the stomach to the small intestine and in which pregelatinized liquid food is fed to the patients.

The above-described methods however involve several problems. In the case where the rate of feeding is decreased, it is necessary to feed liquid food to the patients for many hours; where the amount of liquid food is reduced, the patients may be undernourished; and where liquid food is diluted, it becomes necessary to feed it in a large quantity. Moreover, it is difficult to prevent the patients from vomiting merely by having them sit in a position considered to be appropriate. On the other hand, it is better to avoid using medicines as much as possible. Further, if liquid food is gelatinized, it is necessary to forcibly feed the gelatinized food to the patients. In addition, when attempts are made to supply the pregelatinized food by way of a tube, it tends to clog the tube.

An object of the present invention is therefore to provide antiemetic food products that can prevent patients from suffering from emesis associated with the ingestion of liquid food and that are fit even for intubation feeding.

DISCLOSURE OF THE INVENTION

We made extensive studies in order to solve the aforementioned problems, and, as a result, attained the present invention.

The present invention provides the following:
(1) an antiemetic food product comprising a solution containing one or more thickeners selected from low-methoxyl pectin, sodium alginate, alginic acid, kappa carrageenan, iota carrageenan, lambda carrageenan, and gellan gum;
(2) an antiemetic food product comprising, as one set, a solution containing one or more thickeners selected from low-methoxyl pectin, sodium alginate, alginic acid, kappa carrageenan, iota carrageenan and gellan gum, and a calcium solution;
(3) an antiemetic food product comprising, as one set, a solution containing iota carrageenan, and a magnesium solution;
(4) an antiemetic food product comprising, as one set, a solution containing lambda carrageenan, and a lactoprotein solution;
(5) an antiemetic food product comprising, as one set, a solution containing low-methoxyl pectin, and a calcium solution, the amount of calcium contained in the calcium solution being from 65 to 160 mg for 1 g of the low-methoxyl pectin on dry basis;
(6) an antiemetic food product comprising, as one set, a solution containing iota carrageenan, and a magnesium solution, the amount of magnesium contained in the magnesium solution being from 300 to 700 mg for 1 g of the iota carrageenan on dry basis;
(7) an antiemetic food product comprising, as one set, a solution containing lambda carrageenan, and a lactoprotein solution, the amount of lactoprotein contained in the lactoprotein solution being from 2.5 to 8 g for 1 g of the lambda carrageenan on dry basis; and
(8) an antiemetic food product as described in any of the above items (1) to (7), wherein the thickener-containing solution has a concentration of 1 to 12 w/v %.

The present invention also provides a method for preventing emesis associated with the ingestion of liquid food, comprising feeding one of the antiemetic food products described in the above items (1) to (8) to those patients in need of prevention of emesis associated with the ingestion of liquid food.

The present invention further relates to the use of a solution containing one or more thickeners selected from low-methoxyl pectin, sodium alginate, alginic acid, kappa carrageenan, iota carrageenan, lambda carrageenan and gellan gum for the production of an antiemetic food product useful for preventing emesis associated with the ingestion of liquid food.

BEST MODE FOR CARRYING OUT THE INVENTION (1) Antiemetic Food Products of the Invention The term "antiemetic food products" as used herein means food products that are fed, by means of intubation feeding, to a patient who is undergoing intubation feeding of liquid food, before or after or simultaneously with the feeding of liquid food to prevent the patient from suffering from emesis. A liquid diet is not masticated when it is fed to a patient by means of intubation feeding, and carbohydrates, etc. contained in the liquid diet cannot fully be digested. This is considered to be one reason for the patient to tend to vomit the liquid diet.

In one embodiment of the present invention, there is provided an antiemetic food product capable of preventing emesis of the above-described type, comprising a solution containing one or more thickeners selected from low-methoxyl pectin, sodium alginate, alginic acid, kappa carrageenan, iota carrageenan, lambda carrageenan and gellan gum.

In the present invention, the "low-methoxyl pectin" (hereinafter may be referred to as "LM pectin") refers to pectins having degrees of esterification of not higher than 50%. LM pectin has the property of reacting with calcium to increase viscosity. The present invention utilizes this reaction or property. Namely, in the stomach, LM pectin reacts with calcium contained in liquid food to increase the viscosity of the liquid food, thereby preventing a patient from vomiting. Examples of LM pectin include pectins of citrus fruits such as lemon, lime, orange and grapefruit, and apple pectin. It is suitable to feed such LM pectin in an amount of 3 g or more per 1000 kcal of liquid food or a liquid diet. This is because, as will be clear from the results of Test Examples, which will be described later in this specification, this amount of LM pectin can make the viscosity of the liquid diet appropriate to prevent a patient from vomiting. Preferably, the amount of LM pectin is 6 g or more. Even if the amount of LM pectin is excessively large, the obtainable effect is not increased proportionally. It is therefore appropriate to limit the amount of LM pectin to approximately 30 g.

By the terms "alginic acid" and "sodium alginate (hereinafter may be referred to as "Na alginate")" as herein used are meant hydrophilic colloidal polysaccharides extracted from seaweed. These polysaccharides have the property of reacting with calcium to cause gelling. The present invention utilizes this reaction or property. As will be apparent from the results of Test Examples, it is appropriate to use the polysaccharide in an amount of 6 g or more, preferably 9 g or more for 1000 kcal of a liquid diet. Even if the amount of the polysaccharide is excessively large, the obtainable effect is not increased proportionally, so that it is appropriate to limit the amount of the polysaccharide to approximately 45 g.

In the present invention, "kappa carrageenan", "iota carrageenan" and "lambda carrageenan" refer to carrageenans of the kappa type, iota type and lambda type, respectively. The former two types have the property of reacting with calcium to cause gelling, thereby increasing viscosity. The lambda type has the property of reacting with lactoprotein such as sodium casein, albumin or whey to cause gelling, thereby increasing viscosity. In particular, carrageenan of the iota type has the property of reacting also with magnesium to cause gelling. The present invention utilizes these reactions or properties. As will be clear from the results of Test Examples, it is appropriate to use, for example, iota or lambda carrageenan in an amount of 0.3 g or more, preferably 0.5 g or more for 1000 kcal of a liquid diet. Even if the amount of carrageenan is excessively increased, the obtainable effect is not increased proportionally. It is therefore appropriate to limit the amount of carrageenan to, at most, approximately 2.5 g.

In the present invention, "gellan gum" refers to a polysaccharide produced by *Pseudomonas elodea*. This polysaccharide has the property of reacting with calcium to cause gelling, and can thus increase viscosity. It is therefore possible to use gellan gum in the present invention.

As mentioned previously, the antiemetic food product according to one embodiment of the present invention comprises a solution containing one or more of the above-described thickeners. Any combination of the thickeners can be used. The word "solution" herein means an aqueous solution. In general, clean water is used to prepare the solution. Specifically, the thickener/thickeners is/are dissolved in clean water so that the resulting solution will have a concentration of 1 to 12 w/v %. As can also be seen from the results of Test Examples, this level of concentration is suitable for preventing a patient from vomiting liquid food, and for preventing the solution from clogging a tube in the case where the solution is fed by means of intubation feeding.

Another embodiment of the antiemetic food product comprises, as one set, a solution containing one or more thickeners selected from low-methoxyl pectin, sodium alginate, alginic acid, kappa carrageenan, iota carrageenan and gellan gum, and a calcium solution.

In the case where a liquid diet of low calcium content is fed to a patient, it is preferable to feed a calcium solution separately. In this case, the thickener-containing solution and the calcium solution are combined as one set. By the phrase "to be combined as one set" is meant that separately packed two solutions are formed as one set (kit).

In the present invention, "calcium" in any form can be used as long as it is fit for food. Examples of the calcium include: calcium chloride, calcium acetate, calcium lactate produced by L-form fermentation, synthetic calcium lactate, calcium gluconate, calcium primary phosphate, calcium malate, calcium sulfate, calcium hydroxide, calcium citrate, calcium secondary phosphate, calcium tertiary phosphate, powdered bones, calcium carbonate, shell powder, egg-shell powder, and the like. Of these, calcium chloride, calcium lactate and calcium gluconate are preferred because they are highly soluble in clean water and have high calcium contents. One or more of these calcium sources are dissolved in clean water to form a calcium solution. There is no particular limitation on the concentration of the calcium solution. However, the concentration of the calcium solution is preferably such that calcium will be from 65 to 160 mg for 1 g of LM pectin, and from 50 to 110 mg for 1 g of Na alginate on dry basis. As will be clear from the results of Test Examples, when the concentration of the calcium solution is in the above range, the thickener and calcium react with each other to make the viscosity of liquid food suitable for preventing emesis.

Still another embodiment of the antiemetic food product comprises, as one set, a solution containing iota carrageenan, and a magnesium solution.

Iota carrageenan has the property of reacting also with magnesium to cause gelling. In the case where a liquid diet of low magnesium content is fed to a patient, it is preferable to feed a magnesium solution separately. In the present invention, "magnesium" in any form can be used as long as it is fit for food. Examples of the magnesium include: magnesium chloride, magnesium carbonate, magnesium L-glutamate, magnesium casein, and the like. One or more of these magnesium sources are dissolved in clean water to form a magnesium solution. The magnesium solution can have any concentration. However, the concentration of the magnesium solution is preferably such that magnesium will be from 300 to 700 mg per 1 g of iota carrageenan on dry basis.

Still another embodiment of the antiemetic food product comprises, as one set, a solution containing lambda carrageenan, and a lactoprotein solution.

Lambda carrageenan has the property of reacting with lactoprotein such as sodium casein, albumin or whey to cause gelling. It is therefore possible to provide an antiemetic food product by using a solution containing lambda carrageenan in combination with a lactoprotein solution prepared by dissolving lactoprotein in clean water. In this embodiment, the amount of lactoprotein 2.5 to 8 g for 1 g of lambda carrageenan on dry basis is preferred.

There is no particular limitation on the material for and shape of container to be used for packaging these antiemetic food products of the present invention. Transparent pouches (polyethylene bags), aluminum pouches, etc., for instance, are preferably used for this purpose.

(2) Process for Manufacturing Antiemetic Food Products

A process for manufacturing an antiemetic food product of the present invention will be described hereinafter by referring to the case where an LM pectin solution is used.

Firstly, a solution of LM pectin is prepared. LM pectin is dissolved in clean water; the solution is packed in a desired container; and the container is sealed. Subsequently, if this solution is to be preserved for a long period of time, it is preferable to heat the solution at 105 to 121° C. for 5 to 60 minutes for sterilization. It is noted that, when the pH of the solution has been adjusted to 3–4 by using an edible acid, e.g., citric acid, the heating temperature can be lowered to approximately 90 to 95° C.

Further, in the case of antiemetic food products according to other embodiments of the present invention, where a thickener-containing solution is used in combination with a calcium, magnesium or lactoprotein solution, the latter solution is prepared separately. Namely, calcium, magnesium or lactoprotein is dissolved in clean water; the resulting solution is packed in a desired container; and this container is sealed. If this solution is to be preserved for a long period of time, it is preferable to heat the solution at a temperature of 105 to 121° C. for 5 to 60 minutes for sterilization. The solution obtained in this manner, and a thickener-containing solution, for instance, the above-described LM pectin solution packed in a container, are combined as one set, thereby producing an antiemetic food product of the present invention.

Alternatively, a thickener-containing solution such as an LM pectin solution, and a solution of calcium or the like may be heated to a temperature of preferably 105–121° C. prior to packaging, and aseptically packed in desired separate packages, which are then sealed.

(3) Usage of Antiemetic Food Products of the Invention

The antiemetic food products of the present invention produced according to the aforementioned methods can be fed to those patients who are taking liquid food. In the case where only a thickener-containing solution is used, after feeding the thickener-containing solution, for example, an LM pectin solution, to a patient, a liquid diet that is usually fed to the patient is fed. In the case of an antiemetic food product comprising a thickener-containing solution and a solution of calcium or the like, such as one comprising, as one set, an LM pectin solution and a calcium solution, these two solutions are successively fed to a patient after feeding a liquid diet to the patient. The LM solution and the calcium solution maybe fed in any order. However, in order to prevent the two solutions from reacting with each other and causing coagulation in a tube, it is better to wash the tube by allowing a small amount of clean water to pass through it after feeding one solution and before feeding the other. Another method is such that, after feeding the LM pectin solution to a patient, a liquid diet that has been mixed with the calcium solution is fed. Still another method is such that, after successively feeding the LM pectin solution and a liquid diet to a patient, the calcium solution is fed.

The antiemetic food products of the present invention can thus be fed to those patients who are taking liquid food. The reason why these antiemetic food products can prevent these patients from suffering from emesis is considered to be as follows: a liquid diet and the antiemetic food product are mixed with each other in the stomach, and a polysaccharide such as LM pectin reacts with a cation (calcium, magnesium or the like) contained in the liquid diet or in a cationic solution separately fed to the patients, thereby causing moderate gelling; as a result, the viscosity of the food (liquid diet) contained in the stomach is increased, and the reflux of the food from the stomach or esophagus is prevented; the patients are thus prevented from vomiting.

EXAMPLES

The present invention will now be explained in more detail by referring to the following Examples and Test Examples. It is noted that the unit "%" is "% by weight" in this specification unless otherwise indicated.

Example 1

A 10 w/v % LM pectin solution was packed in aluminum pouches so that each pouch contained 50 ml of the solution. These pouches were sealed and heated at 110° C. for 30 minutes for sterilization to provide an antiemetic food product of the present invention.

To a patient who had been undergoing intubation feeding of a liquid diet three times a day, the total amount of the liquid diet being 1200 kcal/day, and who had been suffering from emesis, the above antiemetic food product of the present invention was fed in the following manner. After injecting one pack of the antiemetic food product of the invention into a tube by using a syringe, one dose of the liquid diet was fed as usual to the patient through the tube. This procedure was repeated for one week. The patient did not vomit at all during this period.

Example 2

A 10 w/v % LM pectin solution was packed in aluminum pouches so that each pouch contained 50 ml of the solution, and these pouches were sealed and heated at 110° C. for 30 minutes for sterilization. Separately, a 1 w/v % calcium chloride solution was packed in aluminum pouches so that each pouch contained 40 ml of the solution, and these pouches were sealed and heated at 110° C. for 30 minutes for sterilization.

The above-prepared LM pectin and calcium solutions were combined as one set to provide an antiemetic food product of the present invention.

To a patient who had been undergoing intubation feeding of a liquid diet three times a day, the total amount of the liquid diet being 1200 kcal/day, and who had been suffering from emesis, the above antiemetic food product of the present invention was fed in the following manner. After injecting one pack of the LM pectin solution into a tube by using a syringe, one dose of the liquid diet was fed as usual to the patient via the tube. One pack of the calcium solution was then fed to the patient. This procedure was repeated for one week. The patient did not vomit at all during this period.

Example 3

A 15 w/v % LM pectin solution was packed in polyethylene bags so that each bag contained 30 ml of the solution, and these bags were sealed and heated at 120° C. for 15 minutes for sterilization. Separately, a 1 w/v % calcium lactate solution was packed in aluminum pouches so that each pouch contained 60 ml of the solution, and these pouches were sealed and heated at 120° C. for 15 minutes for sterilization.

The above-prepared LM pectin and calcium solutions were combined as one set to provide an antiemetic food product of the present invention.

To a patient who had been undergoing intubation feeding of a liquid diet three times a day, the total amount of the liquid diet being 1200 kcal/day, and who had been suffering from emesis, the above antiemetic food product of the present invention was fed in the following manner. 400 kcal (one dose) of the liquid diet was mixed with one pack of the calcium solution. Also, one pack of the LM pectin solution was diluted with 30 ml of clean water. The diluted LM pectin solution was first injected into a tube by using a syringe, and the liquid food mixed with the calcium solution was then fed to the patient via the tube. This procedure was repeated for one week. The patient did not vomit at all during this period.

Example 4

The pH of a 5 w/v % LM pectin solution was first adjusted to 4.0 by using a citric acid solution. This LM pectin solution was then heated at a temperature of 95° or higher for 10 minutes, and hot-packed in aluminum pouches so that each pouch contained 50 ml of the solution. Separately, a 2 w/v % calcium gluconate solution was heated at a temperature of 95° C. or higher for 10 minutes, and then filtered through a filter with a pore size of $0.2\mu$. This solution was aseptically packed in sterilized polyethylene bags so that each bag contained 50 ml of the solution, and these bags were sealed.

The above-prepared LM pectin and calcium solutions were combined as one set to provide an antiemetic food product of the present invention.

This antiemetic food product of the invention was fed to a patient in the same manner as in Example 2. As a result, the patient was successfully prevented from vomiting.

Example 5

A 1 w/v % iota carrageenan solution was packed in aluminum pouches so that each pouch contained 50 ml of the solution. These pouches were sealed and heated at 110° C. for 30 minutes for sterilization to provide an antiemetic food product of the present invention.

To a patient who had been undergoing intubation feeding of a liquid diet (containing 20 mg % of magnesium) three times a day, the total amount of the liquid diet being 1200 kcal/day, and who had been suffering from emesis, the above antiemetic food product of the present invention was fed in the following manner. After injecting one pack of the antiemetic food product of the invention into a tube by using a syringe, one dose of the liquid diet was fed to the patient as usual via the tube. This procedure was repeated for one week. The patient did not vomit at all during this period.

Example 6

A 1 w/v % iota carrageenan solution was packed in aluminum pouches so that each pouch contained 50 ml of the solution, and these pouches were sealed and heated at 110° C. for 30 minutes for sterilization. Separately, a 1 w/v % magnesium chloride solution was packed in aluminum pouches so that each pouch contained 40 ml of the solution, and these pouches were sealed and heated at 110° C. for 30 minutes for sterilization.

The above-prepared iota carrageenan and magnesium solutions were combined as one set to provide an antiemetic food product of the present invention.

To a patient who had been undergoing intubation feeding of a liquid diet (containing 20 mg % of magnesium) three times a day, the total amount of the liquid diet being 1200 kcal/day, and who had been suffering from emesis, the above antiemetic food product of the present invention was fed in the following manner. After injecting one pack of the iota carrageenan solution into a tube by using a syringe, one dose of the liquid diet was fed as usual to the patient via the tube. One pack of the magnesium solution was then fed to the patient. This procedure was repeated for one week. The patient did not vomit at all during this period.

Example 7

A 4 w/v % lambda carrageenan solution was packed in aluminum pouches so that each pouch contained 50 ml of the solution. These pouches were sealed and heated at 110° C. for 30 minutes for sterilization. Separately, a 2.5 w/v % sodium casein solution was packed in aluminum pouches so that each pouch contained 40 ml of the solution, and these pouches were sealed and heated at 110° C. for 30 minutes for sterilization.

The above-prepared lambda carrageenan and sodium casein solutions were combined as one set to provide an antiemetic food product of the present invention.

To a patient who had been undergoing intubation feeding of a liquid diet (containing 1 g % of sodium casein) three times a day, the total amount of the liquid diet being 1200 kcal/day, and who had been suffering from emesis, the above antiemetic food product of the present invention was fed in the following manner. After injecting one pack of the lambda carrageenan solution into a tube by using a syringe, one dose of the liquid diet was fed to the patient as usual via the tube. One pack of the sodium casein solution was then fed to the patient. This procedure was repeated for one week. The patient did not vomit at all during this period.

Example 8

The pH of a 7 w/v % solution of sodium alginate and LM pectin (1:1) was first adjusted to 3.8 by using a citric acid solution. This solution was packed in aluminum pouches so that each pouch contained 50 ml of the solution, and heated at 95° for 10 minutes. Separately, a 5 w/v % calcium gluconate solution was heated at 105°C. for 8 minutes, and then filtered through a filter with a pore size of $0.2\mu$. This solution was aseptically packed in sterilized polyethylene bags so that each bag contained 50 ml of the solution, and these bags were sealed.

The above-prepared solution of sodium alginate+LM pectin (1:1), and calcium solution were combined as one set to provide an antiemetic food product of the present invention.

This antiemetic food product of the present invention was fed to a patient in the same manner as in Example 2. As a result, the patient was prevented from vomiting.

Test Example 1 (Amount of LM Pectin for Liquid Diet)

Test Procedure

To 1000 ml of a commercially available liquid diet (1 kcal/ml; containing 60 mg % of calcium), LM pectin solutions with varying concentrations (w/v %) as shown in Table 1 were respectively added in an amount of 100 ml. The viscosities of these mixtures were measured.

Test Results

The results are as shown in Table 1.

It can be understood from the data shown in the table that, when 3.0 g or more, preferably 6.0 g or more of LM pectin is added to 1000 kcal of the liquid diet, an appropriate viscosity can be obtained.

TABLE 1

| Concentration of LM Pectin Solution (%) | 0.1 | 0.5 | 1 | 2 | 3 | 4 | 5 | 6 | 7 | 8 | 9 | 10 | 11 | 12 |
|---|---|---|---|---|---|---|---|---|---|---|---|---|---|---|
| Amount of LM Pectin (g) | 0.1 | 0.5 | 1 | 2 | 3 | 4 | 5 | 6 | 7 | 8 | 9 | 10 | 11 | 12 |
| Viscosity (mPa · s) | 20 | 60 | 90 | 160 | 320 | 400 | 460 | 800 | 920 | 1,150 | 1,520 | 2,050 | 2,510 | 3,200 |
| Level of Emesis | C | C | C | C | B | B | B | A | A | A | A | A | A | A |

Note 1) The viscosity of the liquid diet was 10 mPa · s.
Note 2) "Amount of LM Pectin" is an amount (g) for 1000 kcal of the liquid diet.
Note 3) "Level of Emesis"
A: Emesis can be prevented substantially completely (7–10 of 10 patients do not vomit).
B: Emesis can be fairly prevented (3–6 of 10 patients do not vomit).
C: Emesis can hardly be prevented (0–2 of 10 patients do not vomit).

Test Example 2 (Amount of Sodium Alginate for Liquid Diet)

Test Procedure

To 1000 ml of a commercially available liquid diet (1 kcal/ml; containing 60 mg % of calcium), sodium alginate solutions with varying concentrations (w/v %) as shown in Table 2 were respectively added in an amount of 100 ml. The viscosities of these mixtures were measured.

Test Results

The results are as shown in Table 2.

The data shown in Table 2 demonstrates that, when 6.0 g or more, preferably 9.0 g or more of sodium alginate is added to 1000 kcal of the liquid diet, an appropriate viscosity can be obtained.

TABLE 2

| Concentration of Sodium Alginate Solution (%) | 0.1 | 0.5 | 1 | 2 | 3 | 4 | 5 | 6 | 7 | 8 | 9 | 10 | 11 | 12 |
|---|---|---|---|---|---|---|---|---|---|---|---|---|---|---|
| Amount of Sodium Alginate (g) | 0.1 | 0.5 | 1 | 2 | 3 | 4 | 5 | 6 | 7 | 8 | 9 | 10 | 11 | 12 |
| Viscosity (mPa · s) | 15 | 30 | 50 | 70 | 100 | 180 | 250 | 320 | 400 | 480 | 750 | 900 | 1,240 | 1,400 |
| Level of Emesis | C | C | C | C | C | C | C | B | B | B | A | A | A | A |

Note 1) The viscosity of the liquid diet was 10 mPa · s.
Note 2) "Amount of Sodium Alginate" is an amount (g) for 1000 kcal of the liquid diet.
Note 3) "Level of Emesis"
A: Emesis can be prevented substantially completely (7–10 of 10 patients do not vomit).
B: Emesis can be fairly prevented (3–6 of 10 patients do not vomit).
C: Emesis can hardly be prevented (0–2 of 10 patients do not vomit).

Test Example 3 (Amount of Iota Carrageenan for Liquid Diet)

Test Procedure

To 1000 ml of a commercially available liquid diet (1 kcal/ml; containing 20 mg % of magnesium), iota carrageenan solutions with varying concentrations (w/v %) as shown in Table 3 were respectively added in an amount of 100 ml. The viscosities of these mixtures were measured.

Test Results

The results are as shown in Table 3.

The data shown in Table 3 demonstrates that, when 0.3 g or more, preferably 0.5 g or more of iota carrageenan is added to 1000 kcal of the liquid diet, an appropriate viscosity can be obtained.

TABLE 3

| Concentration of Iota Carrageenan Solution (%) | 0.1 | 0.3 | 0.5 | 1 | 2 |
|---|---|---|---|---|---|
| Amount of Iota Carrageenan (g) | 0.1 | 0.3 | 0.5 | 1 | 2 |
| Viscosity (mpa · s) | 70 | 350 | 620 | 660 | 960 |
| Level of Emesis | C | B | A | A | A |

Note 1) The viscosity of the liquid diet was 10 mPa · s.
Note 2) "Amount of Iota Carrageenan" is an amount (g) for 1000 kcal of the liquid diet.
Note 3) "Level of Emesis"
A: Emesis can be prevented substantially completely (7–10 of 10 patients do not vomit).
B: Emesis can be fairly prevented (3–6 of 10 patients do not vomit).
C: Emesis can hardly be prevented (0–2 of 10 patients do not vomit).

Test Example 4 (Amount of Lambda Carrageenan for Liquid Diet)

Test Procedure

To 1000 ml of a commercially available liquid diet (1 kcal/ml; containing 3 g % of sodium casein), lambda carrageenan solutions with varying concentrations (w/v %) as shown in Table 4 were respectively added in an amount of 100 ml. The viscosities of these mixtures were measured.

Test Results

The results are as shown in Table 4.

The data shown in Table 4 demonstrates that, when 0.3 g or more, preferably 0.5 g or more of lambda carrageenan is added to 1000 kcal of the liquid diet, an appropriate viscosity can be obtained.

TABLE 4

| Concentration of Lambda Carrageenan Solution (%) | 0.1 | 0.3 | 0.5 | 1 | 2 | 4 | 4 | 5 |
|---|---|---|---|---|---|---|---|---|
| Amount of Lambda Carrageenan (g) | 0.1 | 0.3 | 0.5 | 1 | 2 | 3 | 4 | 5 |
| Viscosity (mPa · s) | 20 | 380 | 510 | 700 | 1200 | 1500 | 1800 | 2200 |
| Level of Emesis | C | B | A | A | A | A | A | A |

Note 1) The viscosity of the liquid diet was 10 mPa · s.
Note 2) "Amount of Lambda Carraeenan" is an amount (g) for 1000 kcal of the liquid diet.
Note 3) "Level of Emesis"
A: Emesis can be prevented substantially completely (7–10 of 10 patients do not vomit).
B: Emesis can be fairly prevented (3–6 of 10 patients do not vomit).
C: Emesis can hardly be prevented (0–2 of 10 patients do not vomit).

Test Example 5 (Amount of Sodium Alginate+LM Pectin for Liquid Diet)

Test Procedure

To 1000 ml of a commercially available liquid diet (1 kcal/ml; containing 60 mg % of calcium), solutions of sodium alginate+LM pectin (2:1) with varying concentrations (w/v %) as shown in Table 5 were respectively added in an amount of 100 ml. The viscosities of these mixtures were measured.

Test Results

The results are as shown in Table 5.

The data shown in Table 5 demonstrates that, when 5.0 g or more, preferably 7.0 g or more of sodium alginate+LM pectin (2:1) is added to 1000 kcal of the liquid diet, an appropriate viscosity can be obtained.

TABLE 5

| Concentration of Solution of Sodium Alginate + LM Pectin (2:1) (%) | 0.1 | 0.5 | 1 | 2 | 3 | 4 | 5 | 6 | 7 | 8 | 9 | 10 | 11 | 12 |
|---|---|---|---|---|---|---|---|---|---|---|---|---|---|---|
| Amount of Sodium Alginate + LM Pectin (2:1) (g) | 0.1 | 0.5 | 1 | 2 | 3 | 4 | 5 | 6 | 7 | 8 | 9 | 10 | 11 | 12 |
| Viscosity (mPa · s) | 10 | 20 | 40 | 80 | 100 | 200 | 300 | 450 | 600 | 700 | 820 | 980 | 1,300 | 1,520 |
| Level of Emesis | C | C | C | C | C | C | B | B | A | A | A | A | A | A |

Note 1) The viscosity of the liquid diet was 10 mPa · s.
Note 2) "Amount of Sodium Alginate + LM Pectin (2:1)" is an amount (g) for 100 kcal of the liquid diet.
Note 3) "Level of Emesis"
A: Emesis can be prevented substantially completely (7–10 of 10 patients do not vomit).
B: Emesis can be fairly prevented (3–6 of 10 patients do not vomit).
C: Emesis can hardly be prevented (0–2 of 10 patients do not vomit).

Test Example 6 (Amount of Calcium for LM Pectin)

Test Procedure

To 1000 ml of a commercially available liquid diet (1 kcal/ml; containing 30 mg % of calcium), 100 ml of an LM pectin solution (5 w/v %) and 100 ml of a calcium solution with one of the concentrations shown in Table 6 were successively added, and the viscosity of the mixture was measured.

Test Results

The results are as shown in Table 6.

The data shown in Table 6 demonstrates that, when the amount of calcium is 65–160 mg, preferably 70–120 mg for 1 g of LM pectin on dry basis, the liquid diet attains an appropriate viscosity level.

TABLE 6

| Concentration of Calcium Solution (mg %) | 0 | 25 | 50 | 100 | 150 | 200 | 250 | 300 | 350 | 400 | 500 |
|---|---|---|---|---|---|---|---|---|---|---|---|
| Amount of Calcium Contained in Calcium Solution (mg) | 0 | 25 | 50 | 100 | 150 | 200 | 250 | 300 | 350 | 400 | 500 |
| Amount of Calcium Contained in Liquid Diet (mg) | 300 | 300 | 300 | 300 | 300 | 300 | 300 | 300 | 300 | 300 | 300 |
| Total Amount of Calcium (mg) | 300 | 325 | 350 | 400 | 450 | 500 | 550 | 600 | 650 | 700 | 800 |
| Amount of Calcium per Gram Unit (mg) | 60 | 65 | 70 | 80 | 90 | 100 | 110 | 120 | 130 | 140 | 160 |
| Viscosity (mPa · s) | 30 | 310 | 510 | 550 | 930 | 2,050 | 1,010 | 570 | 450 | 440 | 390 |
| Level of Emesis | C | B | A | A | A | A | A | A | B | B | B |

Note 1) The viscosity of the liquid diet was 10 mPa · s.
Note 2) "Amount of Calcium per Gram Unit" is an amount (mg) for 1 g of LM pectin on dry basis.
Note 3) "Level of Emesis"
A: Emesis can be prevented substantially completely (7–10 of 10 patients do not vomit).
B: Emesis can be fairly prevented (3–6 of 10 patients do not vomit).
C: Emesis can hardly be prevented (0–2 of 10 patients do not vomit).

Test Example 7 (Amount of Calcium for Sodium Alginate)

Test Procedure

To 1000 ml of a commercially available liquid diet (1 kcal/ml; containing 60 mg % of calcium), 100 ml of a sodium alginate solution (10 w/v %) and 100 ml of a calcium solution with one of the concentrations shown in Table 7 were successively added, and the viscosity of the mixture was measured.

Test Results

The results are as shown in Table 7.

The data shown in Table 7 demonstrates that, when the amount of calcium is 50–110 mg for 1 g of sodium alginate on dry basis, the liquid diet attains an appropriate viscosity level.

TABLE 7

|  | ① | ② | ③ | ④ | ⑤ | ⑥ |
|---|---|---|---|---|---|---|
| Concentration of Calcium Solution (mg %) | 0 | 0 | 0 | 100 | 200 | 500 |
| Amount of Calcium Contained in Calcium Solution (mg) | 0 | 0 | 0 | 100 | 200 | 500 |

TABLE 7-continued

|  | ① | ② | ③ | ④ | ⑤ | ⑥ |
|---|---|---|---|---|---|---|
| Amount of Calcium Contained in Liquid Diet (mg) | 400 | 500 | 600 | 600 | 600 | 600 |
| Total Amount of Calcium (mg) | 400 | 500 | 600 | 700 | 800 | 1,100 |

TABLE 7-continued

|  | ① | ② | ③ | ④ | ⑤ | ⑥ |
|---|---|---|---|---|---|---|
| Amount of Calcium per Gram Unit (mg) | 40 | 50 | 60 | 70 | 80 | 110 |
| Viscosity (mPa · s) | 180 | 560 | 1,560 | 1,650 | 1,840 | 1,790 |
| Level of Emesis | C | A | A | A | A | A |

Note 1) Used 1000 ml of a commercially available liquid diet (1 kcal/ml; containing 60 mg % of calcium) (①: Clean water was added to 667 ml of the liquid diet to a total amount of 1000 ml; ②: Clean water was added to 833 ml of the liquid diet to a total amount of 1000 ml.)
Note 2) "The viscosity of the liquid diet was 10 mPa · s.
Note 3) "Amount of Calcium per Gram Unit" is an amount (mg) for 1 g of sodium alginate on dry basis.
Note 4) "Level of Emesis"
A: Emesis can be prevented substantially completely (7–10 of 10 patients do not vomit).
B: Emesis can be fairly prevented (3–6 of 10 patients do not vomit).
C: Emesis can hardly be prevented (0–2 of 10 patients do not vomit).

Test Example 8 (Amount of Magnesium for Iota Carrageenan)

Test Procedure

To 1000 ml of a commercially available liquid diet (1 kcal/ml; containing 20 mg % of magnesium), 100 ml of an iota carrageenan solution (0.5 w/v %) and 100 ml of a magnesium solution with one of the concentrations shown in Table 8 were successively added, and the viscosity of the mixture was measured.

Test Results

The results are as shown in Table 8.

The data shown in Table 8 demonstrates that, when the amount of magnesium is 300–700 mg, preferably 400–600 mg for 1 g of iota carrageenan on dry basis, the liquid diet attains an appropriate viscosity level.

TABLE 8

|  | ① | ② | ③ | ④ | ⑤ | ⑥ | ⑦ | ⑧ |
|---|---|---|---|---|---|---|---|---|
| Concentration of Magnesium Solution (mg %) | 0 | 0 | 0 | 25 | 50 | 100 | 150 | 200 |
| Amount of Magnesium Contained in Magnesium Solution (mg) | 0 | 0 | 0 | 25 | 50 | 100 | 150 | 200 |
| Amount of Magnesium Contained in Liquid Diet (mg) | 100 | 150 | 200 | 200 | 200 | 200 | 200 | 200 |
| Total Amount of Magnesium (mg) | 200 | 150 | 200 | 225 | 250 | 300 | 350 | 400 |
| Amount of Magnesium per Gram Unit (mg) | 200 | 300 | 400 | 450 | 500 | 600 | 700 | 800 |
| Viscosity (mPa · s) | 180 | 350 | 660 | 660 | 640 | 600 | 470 | 50 |
| Level of Emesis | C | B | A | A | A | A | B | C |

Note 1) Used 1000 ml of a commercially available liquid diet (1 kcal/ml; containing 20 mg % of magnesium) (①: Clean water was added to 500 ml of the liquid diet to a total amount of 1000 ml; ②: Clean water was added to 750 ml of the liquid diet to a total amount of 1000 ml.)
Note 2) "The viscosity of the liquid diet was 10 mPa · s.
Note 3) "Amount of Magnesium per Gram Unit" is an amount (mg) for 1 g of iota carrageenan on dry basis.
Note 4) "Level of Emesis"
A: Emesis can be prevented substantially completely (7–10 of 10 patients do not vomit).
B: Emesis can be fairly prevented (3–6 of 10 patients do not vomit).
C: Emesis can hardly be prevented (0–2 of 10 patients do not vomit).

Test Example 9 (Amount of Lactoprotein for Lambda carrageenan)

Test Procedure

To 1000 ml of a commercially available liquid diet (1 kcal/ml; containing 1 g % of sodium casein), 100 ml of a lambda carrageenan solution (2.5 w/v %) and 100 ml of a sodium casein solution with one of the concentrations shown in Table 9 were successively added, and the viscosity of the mixture was measured.

Test Results

The results are as shown in Table 9.

The data shown in Table 9 demonstrates that, when the amount of sodium casein is 2.5–8 g, preferably 4–8 g for 1 g of lambda carrageenan on dry basis, the liquid diet attains an appropriate viscosity level.

TABLE 9

|  | ① | ② | ③ | ④ | ⑤ | ⑥ | ⑦ |
|---|---|---|---|---|---|---|---|
| Concentration of Sodium Casein Solution (g %) | 0 | 0 | 0 | 0.5 | 2.5 | 5 | 10 |
| Amount of Sodium Casein Contained in Sodium Casein Solution (g) | 0 | 0 | 0 | 0.5 | 2.5 | 5 | 10 |
| Amount of Sodium Casein Contained in Liquid Diet (g) | 5 | 6.7 | 10 | 10 | 10 | 10 | 10 |
| Total Amount of Sodium Casein (g) | 5 | 6.7 | 10 | 10.5 | 12.5 | 10 | 20 |
| Amount of Casein per Gram Unit (mg) | 2 | 2.68 | 4 | 4.2 | 5 | 6 | 8 |
| Viscosity (mPa · s) | 180 | 310 | 1,200 | 1,800 | 2,600 | 3,800 | 7,900 |
| Level of Emesis | C | B | A | A | A | A | A |

Note 1) Used 1000 ml of a commercially available liquid diet (1 kcal/ml; containing 1 mg % of sodium casein) (①: Clean water was added to 500 ml of the liquid diet to a total amount of 1000 ml; ②: Clean water was added to 670 ml of the liquid diet to a total amount of 1000 ml.)
Note 2) "The viscosity of the liquid diet was 10 mPa · s.
Note 3) "Amount of Sodium Casein per Gram Unit" is an amount (g) for 1 g of lambda carrageenan on dry basis.
Note 4) "Level of Emesis"
A: Emesis can be prevented substantially completely (7–10 of 10 patients do not vomit).
B: Emesis can be fairly prevented (3–6 of 10 patients do not vomit).
C: Emesis can hardly be prevented (0–2 of 10 patients do not vomit).

Test Example 10 (Concentration of LM Pectin Solution) Test Procedure

LM pectin solutions with varying concentrations as shown in Table 10 were respectively placed in syringes, and injected into 8 Fr tubes for intubation feeding to determine the fluidity of the solutions.

Test Results

The results are as shown in Table 10.

The data shown in Table 10 demonstrates that an LM pectin solution with a concentration of not more than 12 w/v % can be fed even by means of intubation feeding.

TABLE 10

| Concentration of LM Pectin Solution (w/v %) | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Suitability for Injection | A | A | A | A | A | A | A | A | A | B | B | B | C | C |

Note 1) Symbols in "Suitability for Injection"
A: Injectable without causing any trouble (Viscosity: 100 mPa · s or lower)
B: Injectable, but a little force and time required (Viscosity: 101–200 mPa · s)
C: Unsuitable for injection (Viscosity: higher than 200 mPa · s)

The above test procedure was repeated by using, instead of the above-described LM pectin solution, a sodium alginate solution, a solution of LM pectin+sodium alginate (1:1), or a solution of LM pectin+sodium alginate+lambda carrageenan (1:1). As shown in Tables 11, 12 and 13, the results were the same as those obtained when the LM pectin solution was used.

TABLE 11

| Concentration of Na Alginate Solution (w/v %) | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Suitability for Injection | A | A | A | A | A | A | A | A | A | A | B | B | C | C |

Note 1) Symbols in "Suitability for Injection"
A: Injectable without causing any trouble (Viscosity: 100 mPa · s or lower)
B: Injectable, but a little force and time required (Viscosity: 101–200 mPa · s)
C: Unsuitable for injection (Viscosity: higher than 200 mPa · s)

TABLE 12

| Concentration of Solution of LM Pectine + Na Alginate (1:1) (w/v %) | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Suitability for Injection | A | A | A | A | A | A | A | A | A | A | A | B | C | C |

Note 1) Symbols in "Suitability for Injection"
A: Injectable without causing any trouble (Viscosity: 100 mPa · s or lower)
B: Injectable, but a little force and time required (Viscosity: 101–200 mPa · s)
C: Unsuitable for injection (Viscosity: higher than 200 mPa · s)

TABLE 13

| Concentration of Solution of LM Pectin + Na Alginate + Lambda Carrageenan(1:1:1) (w/v %) | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Suitability for Injection | A | A | A | A | A | A | A | A | B | B | B | B | C | C |

Note 1) Symbols in "Suitability for Injection"
A: Injectable without causing any trouble (Viscosity: 100 mPa · s or lower)
B: Injectable, but a little force and time required (Viscosity: 101–200 mPa · s)
C: Unsuitable for injection (Viscosity: higher than 200 mPa · s)

INDUSTRIAL UTILITY

When the antiemetic food products of the present invention are used, those patients who have frequently vomited can easily and sufficiently ingest nutrition from liquid food without suffering from emesis.

What is claimed is:

1. An antiemetic food product comprising a solution containing one or more thickeners selected from low-methoxyl pectin, sodium alginate, alginic acid, kappa carrageenan, iota carrageenan, lambda carrageenan and gellan gum.

2. An antiemetic food product comprising a solution containing one or more thickeners selected from low-methoxyl pectin, sodium alginate, alginic acid, kappa carrageenan, iota carrageenan and gellan gum, and a calcium solution.

3. An antiemetic food product comprising a solution containing iota carrageenan, and a magnesium solution.

4. An antiemetic food product comprising a solution containing lambda carrageenan, and a lactoprotein solution.

5. An antiemetic food product comprising a solution containing low-methoxyl pectin, and a calcium solution, the amount of calcium contained in the calcium solution being from 65 to 160 mg for 1 g of the low-methoxyl pectin on dry basis.

6. An antiemetic food product comprising a solution containing iota carrageenan, and a magnesium solution, the amount of magnesium contained in the magnesium solution being from 300 to 700 mg for 1 g of the iota carrageenan on dry basis.

7. An antiemetic food product comprising a solution containing lambda carrageenan, and a lactoprotein solution, the amount of lactoprotein contained in the lactoprotein solution being from 2.5 to 8 g for 1 g of the lambda carrageenan on dry basis.

8. An antiemetic food product according to any one of claims 1 to 7, wherein the thickener-containing solution has a concentration of 1 to 12 w/v %.

9. A method for preventing emesis associated with the ingestion of liquid food, comprising feeding an antiemetic food product according to any one of claims 1 to 7 to a patient in need of prevention of emesis associated with the ingestion of liquid food.

10. A method for the use of a solution containing one or more thickeners selected from low-methoxyl pectin, sodium alginate, alginic acid, kappa carrageenan, iota carrageenan, lambda carrageenan and gellan gum for the production of an antiemetic food product useful for preventing emesis associated with the ingestion of liquid food.

11. A method for preventing emesis associated with the ingestion of liquid food, comprising feeding an antiemetic food product according to claim 8 to a patient in need of prevention of emesis associated with the ingestion of liquid food.

* * * * *